US00PP20456P2

(12) United States Plant Patent
Oudolf

(10) Patent No.: US PP20,456 P2
(45) Date of Patent: Nov. 3, 2009

(54) ***SALVIA* PLANT NAMED 'MADELINE'**

(50) Latin Name: ***Salvia* hybrid**
Varietal Denomination: Madeline

(75) Inventor: Petrus Henricus Oudolf, Hummelo (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/221,682

(22) Filed: Aug. 4, 2008

(51) Int. Cl.
*A01H 5/00* (2006.01)

(52) U.S. Cl. ..... Plt./475

(58) Field of Classification Search ..... Plt./475
See application file for complete search history.

*Primary Examiner*—Kent L Bell
(74) *Attorney, Agent, or Firm*—C. A. Whealy

(57) ABSTRACT

A new and distinct cultivar of *Salvia* plant named 'Madeline', characterized by its compact and upright plant habit; strong and vigorous growth habit; freely flowering habit; and dark violet-colored flowers.

2 Drawing Sheets

Botanical designation: *Salvia* hybrid.
Cultivar denomination: 'Madeline'.

BACKGROUND OF THE INVENTION

The present invention relates to a new and distinct cultivar of *Salvia*, botanically known as *Salvia* hybrid and hereinafter referred to by the name 'Madeline'.

The new *Salvia* originated from an open-pollination during the summer of 1999 of an unnamed selection of *Salvia hians*, not patented, as the female, or seed, parent with an unknown selection of *Salvia*, as the male, or pollen, parent. The new *Salvia* was discovered and selected by the Inventor as a single flowering plant from within the progeny of the stated open-pollination grown in a controlled outdoor nursery environment in Hummelo, The Netherlands during the summer of 2000.

Asexual reproduction of the new cultivar by vegetative cuttings in Hummelo, The Netherlands, since the summer of 2000, has shown that the unique features of this new *Salvia* are stable and reproduced true to type in successive generations.

SUMMARY OF THE INVENTION

Plants of the new *Salvia* have not been observed under all possible environmental conditions. The phenotype may vary somewhat with variations in environment such as temperature and light intensity without, however, any variance in genotype.

The following traits have been repeatedly observed and are determined to be the unique characteristics of 'Madeline'. These characteristics in combination distinguish 'Madeline' as a new and distinct cultivar:

1. Compact and upright plant habit.
2. Strong and vigorous growth habit.
3. Freely flowering habit.
4. Dark violet-colored flowers.

Plants of the new *Salvia* can be compared to plants of the female parent selection. Plants of the new *Salvia* differ from plants of the female parent selection in the following characteristics:

1. Plants of the new *Salvia* are more compact than plants of the female parent selection.
2. Plants of the new *Salvia* are more freely flowering than plants of the female parent selection.
3. Plants of the new *Salvia* will reflower after trimming whereas plants of the female parent selection will not reflower after trimming.
4. Plants of the new *Salvia* and the female parent selection differ in flower color.

Plants of the new *Salvia* can be compared to plants of 'Rhapsody in Blue', disclosed in U.S. Plant Pat. No. 15,148. In side-by-side comparisons, plants of the new *Salvia* differed from plants of 'Rhapsody in Blue' in the following characteristics:

1. Plants of the new *Salvia* were more compact than plants of 'Rhapsody in Blue'.
2. Plants of the new *Salvia* and 'Rhapsody in Blue' differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Salvia*.

The photograph on the first sheet comprises a side perspective view of typical flowering plants of 'Madeline' grown in an outdoor nursery.

The photograph at the top of the second sheet is a close-up view of typical flowers of 'Madeline'.

The photograph at the bottom of the sheet is a close-up view of typical leaves of 'Madeline'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the spring in an outdoor nursery in Lisserbroek, The Netherlands. During the production of the plants, day temperatures ranged from 14° C. to 25° C. and night temperatures ranged from 4° C. to 16° C. Plants had been growing for one year when the photographs and description were taken.

Botanical classification: *Salvia hians* 'Madeline'.

Parentage:

*Female, or seed, parent.*—Unnamed selection of *Salvia hians*, not patented.

*Male, or pollen, parent.*—Unknown selection of *Salvia*, not patented.

Propagation:

*Type.*—By softwood cuttings.

*Time to produce a rooted young plant.*—About two months at 16° to 22° C.

*Root description.*—Fine, moderately dense; color, white to dark brown.

Plant description:

*Type.*—Herbaceous perennial.

*Form.*—Upright and somewhat outwardly spreading plant form; uniform broad inverted triangle. Flowers arranged in upright verticillasters on spikes.

*Branching habit.*—Freely basal branching with about ten main stems.

*Growth habit.*—Moderately vigorous.

*Plant height.*—About 62 cm.

*Plant width.*—About 50 cm.

*Lateral branch description.*—Length: About 62 cm. Diameter: About 5 mm. Internode length: About 14 cm. Strength: Strong. Aspect: Mostly upright. Texture: Densely pubescent. Color: Close to 143A; towards the apex, tinged with close to N187A.

Foliage description:

*Arrangement.*—Opposite, simple.

*Length.*—About 14cm.

*Width.*—About 7.5 cm.

*Shape.*—Elongated ovate.

*Apex.*—Acute.

*Base.*—Cordate.

*Margin.*—Crenate; occasionally with a few serrated lobes.

*Texture, upper surface.*—Smooth, glabrous.

*Texture, lower surface.*—Densely pubescent.

*Venation pattern.*—Pinnate.

*Color.*—Developing leaves, upper surface: Darker than 143A. Developing leaves, lower surface: Close to 137B. Fully expanded leaves, upper surface: Close to 137A; venation, close to 144B to 144C. Fully expanded leaves, lower surface: Close to 137C; venation, close to 144C.

*Petiole length.*—About 3 mm.

*Petiole diameter.*—About 4 mm.

*Petiole texture, upper and lower surfaces.*—Pubescent.

*Petiole color, upper and lower surfaces.*—Close to 144B.

Flower description:

*Flower arrangement and shape.*—Single bilabiate flowers arranged in verticillasters in whorls of six on spikes; flowers face mostly outwardly. Freely flowering habit, about 120 flowers per inflorescence.

*Natural flowering season.*—Continuous flowering from mid-May into July in The Netherlands.

*Flower longevity on the plant.*—About five days; flowers not persistent.

*Flower buds.*—Length: About 1 cm. Diameter: About 5 mm. Shape: Obovate. Color: Close to N92B and N92C.

*Inflorescence size.*—Length: About 32 cm. Diameter: About 5.2 cm.

*Flowers.*—Size: About 7 mm by 14 mm. Depth (height): About 2.2 cm.

*Petals.*—Arrangement: Two, fused at the base. Length, upper lip: About 1.8 cm. Length, lower lip: About 1.5 cm. Width, upper lip: About 1 mm. Width, lower lip: About 7 mm. Shape, upper lip: Broadly elliptic; apex, emarginate; base, attenuate; margin, entire. Shape, lower lip: Spatulate; apex, tri-lobed and broadly emarginate; base, attenuate; margin, entire. Texture, upper surface: Smooth, glabrous. Texture, lower surface: Pubescent. Color: Upper lip, when opening and fully opened, upper and lower surfaces: Close to N88A. Lower lip, when opening and fully opened, upper and lower surfaces: Central lobe, close to 155D; margin, close to 93A. Outer lobes, close to N88A.

*Sepals.*—Arrangement: Five sepals fused into a tube. Length: About 9 mm. Width: About 2 mm. Shape: Elliptic. Apex: Acute. Base: Cuneate. Margin: Entire. Texture, upper and lower surfaces: Pubescent. Color, immature, upper surface: Close to 144C; stripes, close to 144A. Color, immature, lower surface: Close to 138A; stripes, close to 139A tinge with purple. Color, mature, upper surface: Close to 144C; stripes, close to 144A. Color, immature, lower surface: Close to 143C; stripes, close to 143A.

*Pedicels.*—Strength: Strong. Length: About 2 mm. Diameter: About 0.5 mm. Aspect: About 45° from vertical. Texture: Pubescent. Color: Close to 143A.

*Reproductive organs.*—Stamens: Quantity per flower: Two. Filament length: About 1.4 cm. Filament color: Close to N88D. Anther shape: Narrowly elliptic. Anther length: About 2.5 mm. Anther color: Close to 183A. Pollen amount: Abundant. Pollen color: Close to 6A. Pistils: Quantity per flower: One. Pistil length: About 2.7 cm. Stigma shape: Cleft, two-parted. Stigma color: Close to 93B. Style length: About 2.5 cm. Style color: Close to 92D. Ovary color: Close to N144A.

*Seed/fruit.*—Seed and fruit production has not been observed.

Disease/pest resistance: Plants of the new *Salvia* have not been noted to be resistant to pathogens and pests common to *Salvia*.

Garden performance: Plants of the new *Salvia* have exhibited good tolerance to rain and wind and have been observed to be hardy to USDA Hardiness Zone 5 and to tolerate high temperatures of 30° C.

It is claimed:

1. A new and distinct *Salvia* plant named 'Madeline' as illustrated and described.

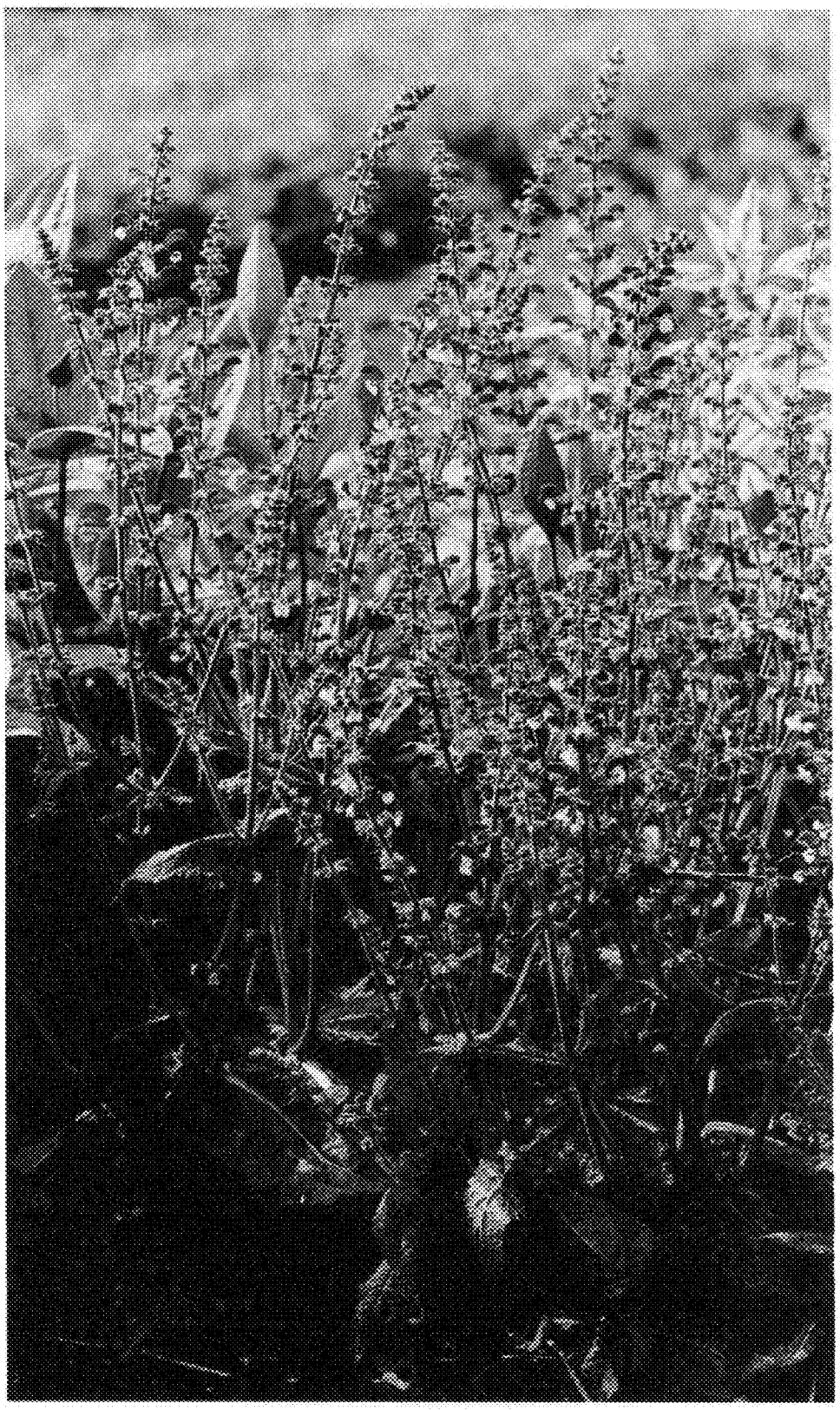

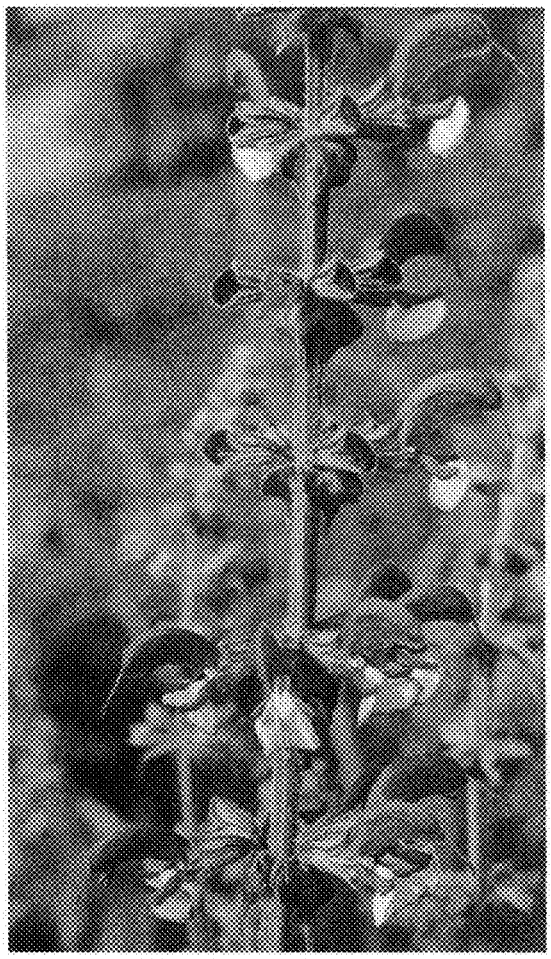
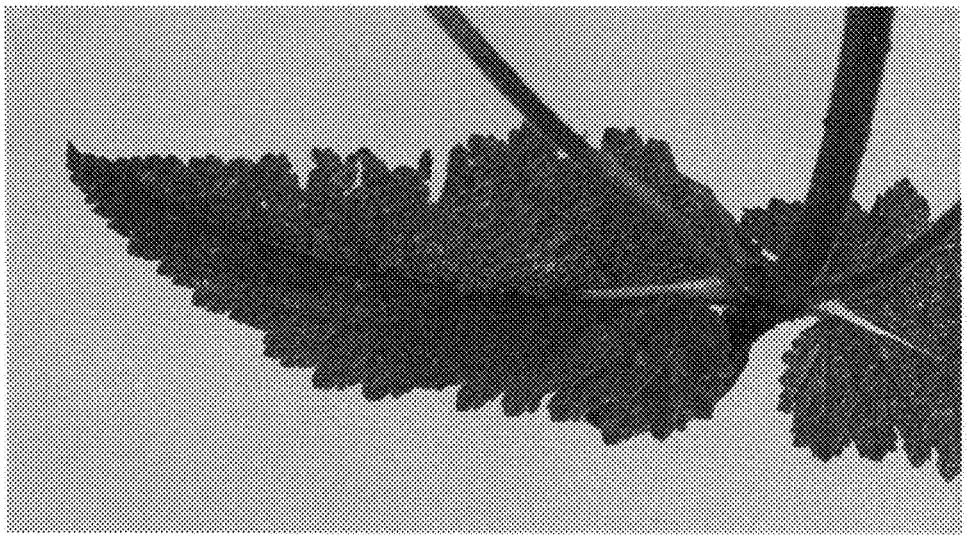

* * * * *